United States Patent [19]

Wolf

[11] Patent Number: 4,570,653

[45] Date of Patent: Feb. 18, 1986

[54] TOOTH CLEANING AND FLOSSING DEVICE

[76] Inventor: James B. Wolf, 3495 Kersdale Rd., Pepper Pike, Ohio 44124

[21] Appl. No.: 647,969

[22] Filed: Sep. 6, 1984

[51] Int. Cl.$^4$ .............................................. A61C 15/00
[52] U.S. Cl. ......................................... 132/91; 132/89
[58] Field of Search .............................. 132/91, 89, 93

[56] References Cited

U.S. PATENT DOCUMENTS

| 361,775 | 4/1887 | Nellis | 132/93 |
|---|---|---|---|
| 1,462,062 | 7/1923 | Browning | 132/93 |
| 1,468,125 | 9/1923 | Nielsen | 132/93 |
| 3,330,732 | 7/1967 | Muhler | 732/89 UX |
| 3,511,249 | 5/1970 | Baitz | 132/89 |

FOREIGN PATENT DOCUMENTS 2519543  7/1983  France .................................. 132/89

Primary Examiner—Gregory E. McNeill
Attorney, Agent, or Firm—Renner, Otto, Boisselle & Lyon

[57] ABSTRACT

The invention relates to a dental device including an elongate structure having opposite parallel sides, each side having a leading edge surface for wiping against a tooth surface or gum surface, each side having an outer surface for simultaneously wiping against the proximal surfaces of respective teeth, the structure being resilient causing the outer surfaces to be resiliently urged against proximal areas of respective teeth, and a foam, abrasive, or adhesive material on part of each of the opposite sides of the structure. The invention also relates to methods for treating or cleaning teeth or gums.

20 Claims, 6 Drawing Figures

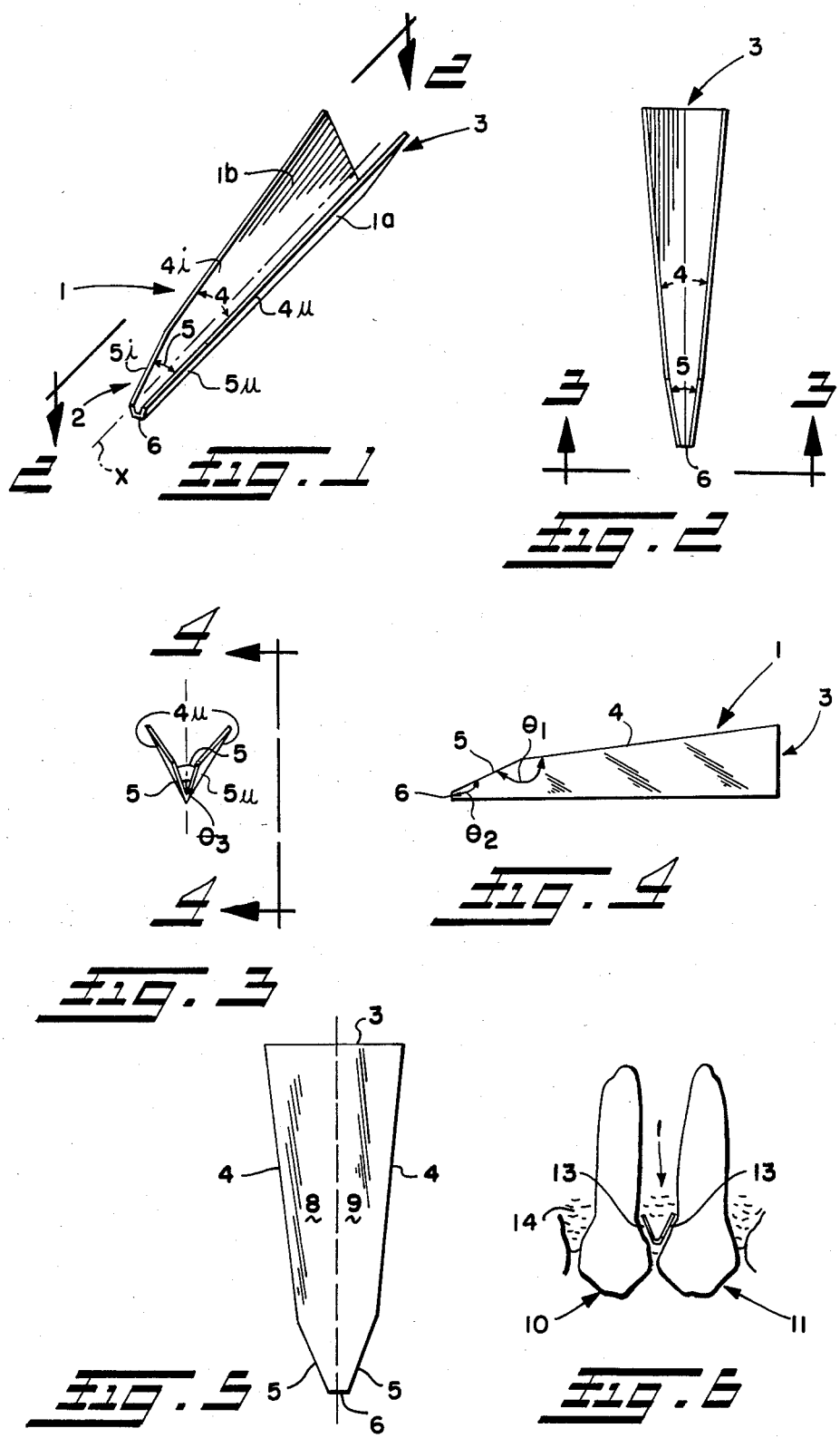

TOOTH CLEANING AND FLOSSING DEVICE

TECHNICAL FIELD

The present invention relates to devices for oral hygiene and treatment. Specifically, the invention relates to apparatus for cleaning and treating proximal surfaces of teeth and adjacent the gums and in the preferred form a device which may apply different materials and medicines to said areas.

BACKGROUND OF PRIOR ART

The cleaning and treatment of areas between teeth has been accomplished by various devices in the past. In addition to the toothbrush, which is not always effective in cleaning the teeth below the gum line and between the teeth, toothpicks made of various materials are used. While these devices are useful for cleaning between the teeth, they are of little value in cleaning below the gum line. Dental floss specifically overcomes the difficulty in cleaning below the gum line, but dental floss is inconvenient and time consuming for proper use.

Moreover, a disadvantage of all of the above devices is the inability thereof to apply a variety of materials below the gum line. Furthermore, stimulation and cleaning of the teeth below the gum line with rigid toothpick devices can be injurious to the user.

The present invention overcomes the above disadvantages by allowing two adjacent gum-tooth interfaces to be safely and expeditiously cleaned or treated simultaneously. Also the invention is considerably less costly and more effective than prior art devices intended to treat gum-tooth interfaces with medicines.

SUMMARY OF THE INVENTION

Briefly, the invention relates to an oral hygiene device, especially for cleaning and treating the interfaces between tooth and gum which are between adjacent teeth and to methods for effecting such cleaning and treatment.

The invention, for example, may be formed of a generally elongate structure, which has an angularity, e.g. a fold, about the axis to provide a pair of surfaces capable respectively of simultaneously wiping the proximal surfaces; the front of the device (the operative end) preferably tapers to a truncated V shape to facilitate insertion between teeth while such surfaces effect wiping.

The V-shape edges or surfaces forming the respective sides of the device may be coated with an adhesive material so that an abrasive material for cleaning, a medicine for treatment, etc., may be retained and thereby applied to the interfaces between tooth and gum.

The material from which the invention is formed should be resilient enough to enable the device to be compressed about the axis upon insertion while the resilient force urges the wiping surfaces against the proximal surfaces for wiping; such resiliency also helps to prevent injury to the user. The device should be rigid enough, though, to allow easy insertion between tooth and gum.

Objectives of the invention include the simultaneous cleaning or treatment of the tooth-gum interfaces between two adjacent teeth; to do so in a manner which is safer and more efficient than previously known; and to do so with a device which is inexpensive, easy to use and disposable after each use. A further objective achieved by the invention is the ability to use either abrasive material embedded in an adhesive attached to the V-shape edges of the device to clean the peridontal areas or to use medical preparations which adhere to the adhesive and which may be topically applied.

It is envisioned that the invention either will be held and inserted between the teeth and gums with the fingers of one hand or will be retained in a non-disposable holder that would facilitate manipulation and use of the device.

BRIEF DESCRIPTION OF DRAWING

In the annexed drawing:

FIG. 1 is a perspective view of the tooth cleaning and flossing device illustrating the V-shape configuration of the front of the device;

FIG. 2 is a top plan view of the device looking in the general direction of arrows 2—2 of FIG. 1;

FIG. 3 is a front elevation of the device looking in the general direction of arrows 3—3 of FIG. 2;

FIG. 4 is a side elevation of the device looking in the general direction of arrows 4—4 of FIG. 3 illustrating the V shape configuration;

FIG. 5 is an illustrative drawing showing the device as it would appear if it were unrolled into a two-dimensional plane; and FIG. 6 is a perspective drawing of the device in use.

DESCRIPTION OF THE PREFERRED EMBODIMENT

Referring now in detail to the drawing, like numerals herein designate like numbered parts in the figures.

In FIG. 1, the tooth cleaning and flossing device, in accordance with the present invention, is generally indicated at 1, having a leading or operative end 2 and a trailing or manipulating end 3. The device 1 is constructed from one continuous piece of resilient material such as plastic or rubber and, as is shown in FIGS. 1, 2 and 3, has inner and outer operative surfaces 4$i$, 5$i$ and 4$u$, 5$u$ joined respectively at edges 4 and 5. Edges 4 and 5 extend generally axially along the length of the device. Inner and outer operative surfaces 4$i$, 5$i$ and 4$u$, 5$u$ and edges 4 and 5 may be selectively coated with an adhesive material, foam material, abrasive material, and/or other material or combination thereof, e.g. to enhance cleaning/wiping, to facilitate application of medicine or other materials, for example to treat gums, etc. The respective edges and surfaces are on each generally elongate side 1$a$, 1$b$ of the device 1 which are generally parallel to the axis X of the device.

The device 1 can best be visualized as an elongate structure having the sides 1$a$, 1$b$, which have been cut by imaginary planes that are coincident with edges 4 and 5 and top edge 6 in FIG. 4 and parallel to and rotated about an axis perpendicular to the longitudinal axis X of the device. This results in a device 1 which tapers to a truncated V-shape at leading or operative end 2. The truncated V-shape of operative end 2 promotes effective use and facilitates use of the device. The further the device is inserted along its longitudinal axis X, the deeper will be the penetration of operative surfaces 4$i$, 5$i$, 4$u$, 5$u$ and edges 4 and 5 toward the root surfaces of the teeth and into the gum line. Therefore, effective cleaning or treatment can be accomplished regardless of whether the user has healthy gums that are fairly normal in shape, has large gaps between the teeth or has peridontal disease or gum recession. The leading or operative end 2 of device 1 is truncated at the tip 6, as is shown in FIGS. 2 and 4, for ease of insertion and to prevent the device 1 from bending during insertion between a pair of adjacent teeth. Insertion of device 1 between two teeth would ordinarily be deep enough so that the truncated tip 6 would protrude between the two teeth on the lingual or palatal side of the teeth.

In FIG. 5, device 1 is illustrated in opened out form against the usual tendency of the device to fold into a generally more V-shape form to illustrate the shape of halves 8 and 9 on sides 1a, 1b.

The angles between edges 4 and 5, and edges 5 and 6 in FIG. 4 and opposing edges 5 in FIG. 3 are not critical. However, the angle between edges 4 and 5, indicated as $\theta_1$ in FIG. 4 preferably is less than 180° but greater than 90° both to facilitate insertion and penetration. The angle between edges 5 and 6, indicated as $\theta_2$ in FIG. 4, preferably is less than 90° but greater than 45° to facilitate insertion of the device. The angle between opposing edges 5, indicates as $\theta_3$ in FIG. 3 preferably is less than 90° but greater than 45° to achieve the desired V-shape of the leading end.

In the preferred embodiment edges 4, 5 and adjacent corresponding surfaces e.g. 4i, 5i, 4u, 5u and tip edge 6 at the operative end 2, are coated with a foam material to enhance wiping action; the foam preferably is resilient, e.g. polyurethane foam, to conform to the tooth surfaces. The foam also may be used for holding medical preparations or such medicament may be distributed directly on the device without foam for application to the interfaces between the teeth and gums of two juxtapositioned teeth as is shown in FIG. 6 or for application directly to gum areas. The adhesive material performs multiple functions. These functions include bonding to operative surfaces 4i, 5i, 4u, 5u and edges 4 and 5 a bristle-type or foam material for cleaning the interproximal areas between teeth. An abrasive material may be applied to the outer operative surfaces of the device for shaping or smoothing fillings. Alternatively, the adhesive may function to bond to said operative surfaces of foam to absorb medicines for treatment such as fluoride, antiseptics or topical anesthetics in preparation for professional prophylaxis. A further function performed by the adhesive is to protect the device from premature wearing and to protect the user from being cut in the event a sharp edge might become honed. An example of adhesive material may also include a foam or foam-like material. Also, the adhesive material itself may be used to perform adequate rubbing and/or abrasive action. Further, if desired, the adhesive material may be eliminated.

In using the device 1 of the invention, end 3 is grasped with the fingers of one hand, or is retained in a specially provided holder (not shown). Such holder or handle would be attached to trailing or manipulating end 3 of the device to facilitate handling of device 1 in the mouth and also to provide additional safety by preventing inadvertent aspiration or swalling of the device. By either turning the handle, or rotating the device on the handle, the invention could be used on both sides, top and bottom, of the mouth.

In either case the user would insert the V-shape, operative end 2 between adjacent teeth 10, 11 as is illustrated in FIG. 6. Operative edges 4 and 5 and corresponding adjacent surfaces 4i, 5i, 4u, 5u will engage the interfaces 12, 13 between tooth (10, 11) and gum 14 and, depending on the mode of use, will either clean or treat the interfaces.

In the cleaning mode, the device 1 preferably has a foam material embedded in an adhesive which coats edges 4 and 5 and the corresponding adjacent surfaces 4i, 5i, 4u and 5u of the device. After inserting the device, the user would move the same in an oscillatory, i.e. back and forth, motion, axially along the length of the device, so as to effect a wiping or cleaning action similar to that experienced when using dental floss, except that the invention will clean two adjacent gumtooth interfaces simultaneously whereas dental floss cleans only one. The resilient character of the invention will prevent over-abrasion of the gum-tooth interfaces 12, 13 during use and yet will provide sufficient rigidity to effect good cleaning.

In the treatment mode, the device 1 would have operative edges 4, 5, 4i, 5i, 4u, and 5u and the corresponding adjacent surfaces coated with a foam. However, the user would introduce the appropriate medicine onto the foam surface. The user would then insert the device 1 and leave the device in place for the recommended treatment time, e.g. in the manner illustrated in FIG. 6. In the event that the device is used to apply fluoride gel, or any other medicine which requires a similar treatment time, to the interproximal areas, fluoride trays could simultaneously be used over the device so that the occlusal surfaces could be treated concurrently. The resilient character of the device will prevent the device from moving after insertion. After treatment has been completed, the device may be removed and discarded.

A part of the device may be made with radio-opaque material so that it can be seen by X-ray. Therefore, in the event the device were inadvertently aspirated or swallowed, it could be readily located.

In view of the foregoing, it will be appreciated that the device 1 in accordance with the invention may be used for a variety of purposes associated with dental hygiene. The device conveniently conforms to the space available between adjacent teeth and during insertion, due to the shape and resiliency of the device, the device tends to penetrate into and beneath the gum line adjacent respectively adjacent teeth. Without coating the device with any other material, the same may be employed for purposes similar to that with which dental floss ordinarily is used, such as cleaning and exercising the gum area, etc. Coating the device with an abrasive material tends to accentuate the cleaning and exercising functions. Moreover, the device may be coated or covered with or may carry a fluoride type material intended for the usual treating purpose, but using the device such material may be most efficiently inserted to very difficult to access locations. In an exemplary case, the device 1 may be dipped into a professional strength fluoride gel and then inserted in each interproximal space. So inserted, the device and floride gel may be left in place for approximately four minutes. Such use would tend to prevent interproximal decay if used with regular frequency, such as every six months, as often now is done with fluoride trays. Also a desensitizing agent could be applied to the device to desensitize the interproximal tooth surfaces. Still further, since the device is relatively inoffensive in appearance and feel during use, the device 1 may have foam applied to the insside surfaces to hold and to apply an anesthesia type material, such as a topical anesthetic; the device with such material thereon may be placed interproximally to anesthetize the gum tissue before professional prophylaxis, etc. Such use would decrease sensitivity, especially for patients who dread prophylaxis because of discomfort. Other medicaments also may be applied using the device such as peroxide and baking soda solution.

STATEMENT OF INDUSTRIAL APPLICATION

The device 1 may be used, accordingly, employing the inner surfaces of the device to treat the proximal surfaces of the teeth, e.g. for wiping plaque daily off teeth, for professional or patient application of fluorides to proximal surfaces, and for professional or patient application of desensitizing agent; and employing the outer surfaces of the device to treat adjacent gum surfaces, e.g. for applying medicaments to gum and for applying topical anesthetic before scaling.

I claim:

1. A dental device, comprising an elongate structure having opposite sides oriented generally in parallel with respect to an elongate axis and angularly with respect to each other, each side having a leading edge surface inclined to such elongate axis for wiping against at least one of a tooth surface and relatively adjacent gum, each side having an outer surface, said outer surfaces being positioned for simultaneously wiping against the proximal surfaces of respective teeth, and said structure having a resiliency characteristic, whereby said outside surfaces are resiliently urged against respective proximal areas of respective teeth during use; and at least one of a foam material, abrasive material or adhesive material on at least part of each of said opposite sides of said structure.

2. The device of claim 1, wherein said opposite sides are folded relative to each other along such axis.

3. The device of claim 1, wherein each of said sides has a curvature generally oriented about an axis extending parallel to such elongate axis.

4. The device of claim 1, each side having an inner surface for engagement with a portion of gum when the device is inserted between a pair of relatively adjacent teeth in the mouth of a patient.

5. The device of claim 4, further comprising medicament on said inner surfaces for application thereby to gum.

6. The device of claim 1, further comprising medicament on said outside surfaces for application to teeth upon insertion in the mouth of a patient.

7. The device of claim 1, further comprising fluoride on said outside surfaces for application to teeth upon insertion in the mouth of a patient.

8. The device of claim 1, said structure having a tapered leading end to facilitate insertion between a pair of relatively adjacent teeth in the mouth of a patient.

9. The device of claim 8, further comprising a blunt tip at said leading end to reduce the tendency of the device to bend upon insertion.

10. The device of claim 1, wherein said opposites sides form a generally V-shape structure.

11. The device of claim 1, comprising foam material on at least part of each of said opposite sides of the device.

12. The device of claim 11, wherein said foam material is on said outside surfaces to conform to the shape of wiped surfaces of teeth during use of the device.

13. The device of claim 11, said foam material being adapted to retain medicament, fluoride and the like.

14. The device of claim 1, comprising abrasive material on at least part of each of said sides to increase the wiping function thereof during use of the device.

15. The device of claim 1, comprising adhesive material on at least part of each of said sides for adhering another material thereto.

16. A method of cleaning teeth comprising inserting between a pair of relatively adjacent teeth in the mouth of a patient proximate the gum line an elongate structure having opposite sides oriented generally in parallel with respect to an elongate axis and angularly with respect to each other, with such opposite sides straddling the gum papilla and extending apically down the sides of the relatively adjacent teeth, each side having a surface for wiping against at least one of a tooth surface and relatively adjacent gum, each side having an outer surface, said outer surfaces being positioned for simultaneously wiping against the proximal surfaces of respective teeth, and said structure having a resiliency characteristic, whereby said outside surfaces are resiliently urged against respective proximal areas of respective teeth during use, and moving said structure generally linearly back and forth while said outside surfaces simultaneously wipe and clean such proximal areas of respective teeth with which engagement is made.

17. A method of treating teeth, comprising applying medicament to a device which includes an elongate structure having opposite sides oriented generally in parallel with respect to an elongate axis and angularly with respect to each other, each side having a surface for wiping against at least one of a tooth surface and relatively adjacent gum, each side having an outer surface, said outer surfaces bing positioned for simultaneously wiping against the proximal surfaces of respective teeth and including on at least a part thereof a foam material in which the medicament is retained, and said structure having a resiliency characteristic, whereby said outside surfaces are resiliently urged against respective proximal areas of respective teeth during use, inserting such structure between a pair of relatively adjacent teeth in the mouth of a patient approximately at the gum line whereby such medicament is applied by the foam material against portions of respective teeth simultaneously.

18. A method of treating gums comprising applying medicament to a device including an elongate structure having opposite sides oriented generally in parallel with respect to an elongate axis and angularly with respect to each other, each side having a surface for wiping against at least one of a tooth surface and relatively adjacent gum, each side having an outer surface, said outer surfaces being positioned for simultaneously wiping against the proximal surfaces of respective teeth, and said structure having a resiliency characteristic, whereby said outside surfaces are resiliently urged against respective proximal areas of respective teeth during use, such device including relatively inner surfaces including therebetween a foam material intended for engagement with gum while the device is inserted between a pair of relatively adjacent teeth, such foam material retaining medicament applied to the device, and inserting the device between a pair of relatively adjacent teeth in the mouth of a patient at least approximately at the gum line, whereby such foam material engages the gum to keep medicament against the gum.

19. The device of claim 13, wherein said foam material is on inside surfaces of said opposite sides of the device for use in applying medicament to gum tissue between teeth.

20. A dental device, comprising an elongate structure having opposite sides oriented generally in parallel with respect to an elongate axis and angularly with respect to each other, each side having a leading edge surface inclined to such elongate axis for wiping against at least one of a tooth surface and relatively adjacent gum, each side having an outer surface, said outer surfaces being positioned for simultaneously wiping against the proximal surfaces of respective teeth, and said structure having a resiliency characteristic, whereby said outside surfaces are resiliently urged against respective proximal areas of respective teeth during use, and said leading edge surfaces converging to a blunt tip at the leading end of said structure.

* * * * *